(12) United States Patent
Kataoka et al.

(10) Patent No.: US 6,438,305 B1
(45) Date of Patent: Aug. 20, 2002

(54) LASER TRANSMITTING SYSTEM AND HAND INSTRUMENT HAVING SUCH SYSTEM FOR USE WITH LASER DEVICE

(75) Inventors: Kenzo Kataoka; Masaki Odaka, both of Kyoto (JP)

(73) Assignee: J. Morita Manufacturing Corporation, Kyoto (JP)

(*) Notice: Subject to any disclaimer, the term of this patent is extended or adjusted under 35 U.S.C. 154(b) by 0 days.

(21) Appl. No.: 09/221,809

(22) Filed: Dec. 29, 1998

(30) Foreign Application Priority Data

Dec. 29, 1997 (JP) .............................. 9-367532

(51) Int. Cl.[7] .................... G02B 6/02; A61B 18/18
(52) U.S. Cl. ...................... 385/125; 606/15; 606/16
(58) Field of Search .................... 385/125, 147, 385/33; 606/13, 14–17, 19, 10; 433/29

(56) References Cited

U.S. PATENT DOCUMENTS

| 3,821,510 A | * | 6/1974 | Muncheryan |
| 5,051,558 A | | 9/1991 | Sukhman |
| 5,374,266 A | * | 12/1994 | Kataoka et al. ............... 606/15 |
| 5,729,646 A | | 3/1998 | Miyagi et al. |
| 5,825,958 A | * | 10/1998 | Gollihar et al. ............. 385/125 |

FOREIGN PATENT DOCUMENTS

| DE | 4227803 A1 | 2/1993 |
| DE | 4006148 C2 | 4/1993 |
| JP | 09-135847 | 5/1997 |
| WO | WO 96/30157 | 10/1996 |

* cited by examiner

*Primary Examiner*—Frank G. Font
*Assistant Examiner*—Amanda Merlino
(74) *Attorney, Agent, or Firm*—Koda & Androlia

(57) ABSTRACT

A laser device includes first and second laser transmitting passages. The first laser transmitting passage in the form of tube has an interior opened at its first and second ends. The second laser transmitting passage has first and second ends. The first end of the second laser transmitting passage is spaced away from but optically connected with the second end of the first laser transmitting passage. This allows that laser transmitted through the first laser transmitting passage is guided into the second laser transmitting passage. Air, on the other hand, is transmitted through the first laser transmitting passage to impinge on the first end of the second laser transmitting passage for cooling.

9 Claims, 6 Drawing Sheets

LASER TRANSMITTING SYSTEM AND HAND INSTRUMENT HAVING SUCH SYSTEM FOR USE WITH LASER DEVICE

FIELD OF THE INVENTION

The present invention relates to a laser transmitting system for use with a laser device for medical or dental procedures, for example, and a hand instrument for use with such laser device.

BACKGROUND OF THE INVENTION

Laser has been used not only in various industrial devices but also in many medical and dental devices. Generally, each of medical and dental devices using laser includes a laser generator for generating laser, an instrument (e.g., hand instrument) for guiding and then emitting laser toward a desired surgical site, and a laser transmitting system, connecting between the laser generator and the instrument for transmitting laser from the laser generator to the instrument.

Mechanicallly, the laser transmitting system can be classified into two transmitting stations; a first transmitting station for guiding laser from the laser generator to the instrument and a second transmitting station for guiding laser in the instrument toward the surgical site. In particular, a variety of improvements have been proposed so far for the second transmitting station.

In the meantime, the second transmitting station may be brought into contact with the surgical site and thereby contaminated or damaged. Accordingly, the second transmitting station is considered to be a consumable article and, in fact, is structured so that it is exchangeable in many such laser devices. The exchangeability of the second transmitting station is also desired from its various purposes.

In such laser devices having first and second separate transmitting stations, when laser is being transmitted from the first to the second transmitting station, it impinges in part against a part of inlet edge of the second transmitting station, thereby heating and then deteriorating such part. Disadvantageously, this will shorten a durability of the second station considerably. To make the matter worse, foreign substances such as dust possibly adhered to the inlet edge of the second transmitting station will accelerate its heating.

To prevent this, in many devices using laser, a tube is provided for the first transmitting station so that air can be provided on the inlet for cooling. Indeed, this is advantageous to prevent the inlet from being overheated too much. However, this requires an additional air supply tube to be used only for cooling along the first transmitting station, which makes the whole transmitting system complicate in structure.

SUMMARY OF THE INVENTION

Accordingly, a laser transmitting system, laser device, and hand instrument for use in such laser device includes a first laser transmitting passage, made from an optical hollow waveguide, including therein an interior opened at first and second ends of the first laser transmitting passage. The device further includes a second laser transmitting passage having a first end and a second end. The first end of the second laser transmitting passage is spaced away but optically connected with the second end of the first laser transmitting passage. This allows that laser transmitted through the first laser transmitting passage is guided into the second laser transmitting passage, and air is transmitted through the first laser transmitting passage to impinge on the first end of the second laser transmitting passage.

With the laser transmitting system of the present invention, since the air is transported through the first laser transmitting passage or tube, no additional passage is needed only for transporting. This simplifies the mechanical structure of a laser device or hand instrument.

In another aspect of the present invention, the laser transmitting system includes an optical member positioned between the second end of the first laser transmitting passage and the first end of the second laser transmitting passage for guiding the laser transmitted from the second end of the first laser transmitting passage into the first end of the second laser transmitting passage. Further, the device has an air passage defining a first chamber enclosing therein the second end of the first laser transmitting passage, a second chamber enclosing therein the first end of the laser transmitting passage, and a passageway fluidly connecting between the first and second chambers so that the air discharged from the second end of the laser transmitting passage is guided through the first chamber, the passageway, and the second chamber to the first end of the laser transmitting passage.

This allows that laser from the first laser transmitting passage is effectively guided to the first end of the second laser transmitting passage. Also, the first end of the second laser transmitting passage, which is heated by laser, is cooled down effectively by the air transported through the first laser transmitting passage.

In another aspect of the present invention, the laser transmitting system includes an air passage having first and second ends. The first end of the air passage is positioned adjacent the first end of the second laser transmitting passage and the second end of the air passage is positioned adjacent the second end of the second laser transmitting passage. This allows that the air impinged on the first end of the laser transmitting passage is guided into the air passage and then discharged to the second end of the second laser transmitting passage.

A hand instrument and laser device includes a cylindrical casing in which the laser transmitting system is included. Also, the air passage is in part defined between the cylindrical casing and the first laser transmitting passage. This arrangement can reduce the number of tubes that should be incorporated in the hand instrument. The hand instrument may include another air passage extending along the first and second laser transmitting passage and toward the second end of the second laser transmitting passage. This allows the air to be discharged toward the second end of the second laser transmitting passage.

DETAILED DESCRIPTION OF THE PREFERRED EMBODIMENTS

Figure 1:
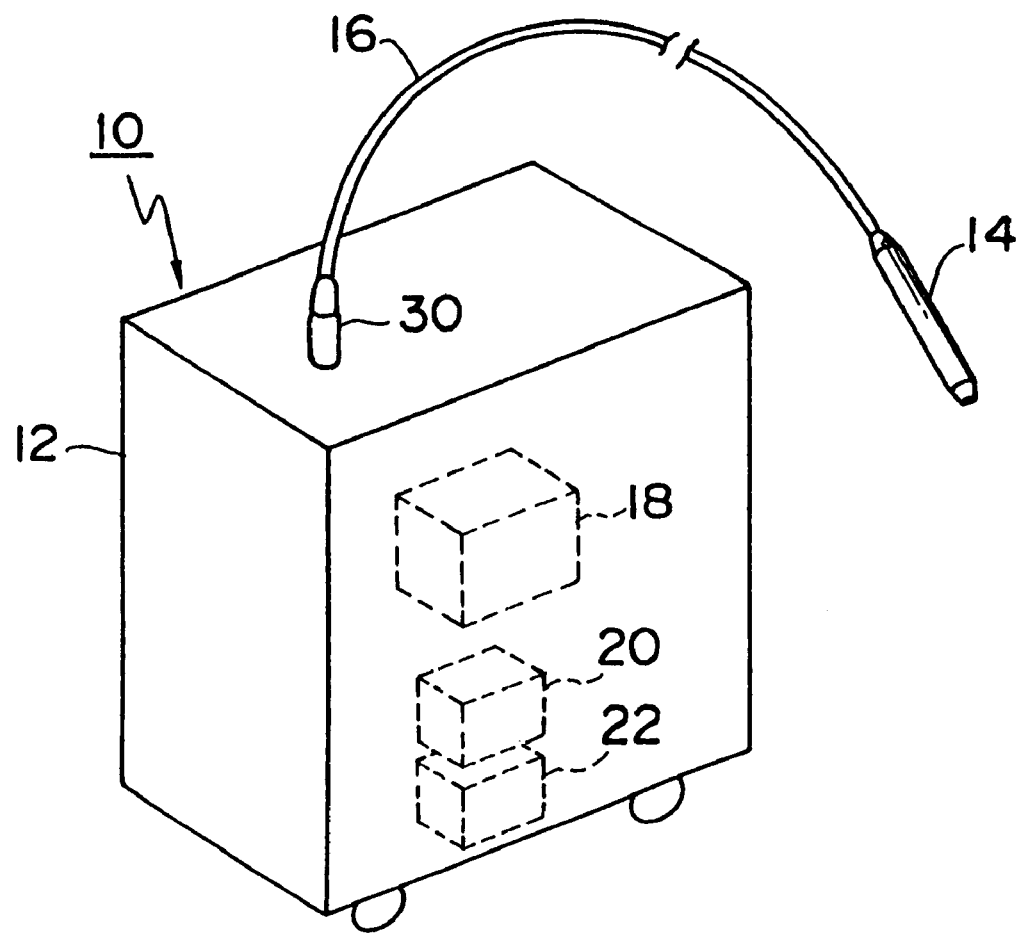
FIG. 1 is a perspective view of a medical device, in which a laser transmitting system of the present invention is incorporated.

Referring to the drawings, particularly in FIG. 1, there is shown an outline of a medical device that uses laser for treatment, generally indicated by reference numeral 10. It should be noted that the term "medical device" includes not only medical device but also dental device throughout this specification. It should also be noted that the present invention is not limited to the medical device and it is equally applicable to various devices that use laser.

The medical device 10 has a laser unit 12 in which laser is generated, a hand instrument 14 that an operator can hold it to direct laser toward a desired surgical site, and a flexible supply tube 16 that connects between the laser unit 12 and the hand instrument 14 for transmitting laser and other materials from the laser unit 12 to the hand instrument 14. The laser unit 12 includes a laser generator 18 for generating laser and pumps 20 and 22 for feeding air and water, respectively, through the flexible supply tube 16 to the hand instrument 14.

Advantageously, laser generated in the laser generator 18 has a wavelength of about 1 to 10 $\mu$m, preferably including Er:YAG laser having a wavelength of 2.94 $\mu$m and/or Nd:YAG laser having a wavelength of 1.06 $\mu$m, for example.

FIG. 2A shows a cross section of a connecting unit 30 that connects between the laser unit 12 and a proximal end of the flexible supply tube 16. The connecting unit 30 has four cylindrical connecting members; first connector 32, second connector 34, third connector 36, and fourth connector 38, connected in series in this order. Preferably, an O-ring is provided at each contact region of between opposing surfaces of the neighboring connectors, forming an airtight seal therebetween.

The first connector 32 is secured to the laser unit 12 at its proximal end positioned adjacent the laser unit 12. A cylindrical connecting piece 32 is secured at its one end to the first connector 32 and is fluidly connected at its opposite end to the air pump 20 (see FIG. 1) to feed air for drying and cooling. The distal end of the connecting piece 40 secured to the first connector 32 is fluidly connected through a passage defined in the first connector 32, circumferential passage 44 defined between the first and second connectors, 32 and 34, and passage 46 defined in the second connector 34 adjacent the proximal end thereof, in the vicinity of the laser unit 12, to a passage 48 extending along a longitudinal axis of the second connector 34. The passage 48 is closed at its proximal end by a transparent window 50 preferably secured with a fixing member 52. Formed in the second connector 34 near the distal end of the passage 48, i.e., adjacent the hand instrument 14, is a reduced portion 54 defining a central portion thereof. A tube or ferrule 56 is securely inserted in the reduced portion 54. The ferrule 56 holds a proximal end portion of a hollow member or tube 58 having an elongated interior 581 so that the interior 581 is fluidly connected with the passage 48. Preferably, the tube 58 is an optical hollow waveguide disclosed in the U.S. Pat. No. 5,729,646 which in entirely incorporated herein by reference.

The first connector 32 is provided with another cylindrical connecting piece 60 to feed air to be discharged to the surgical site. One end of the connecting piece 60 is fluidly connected with the air pump 20. The opposite end of the connecting piece 60 secured to the first connector 32 is fluidly connected through a passage 62 defined in the first connector 32, a circumferential passage 62 defined between the first and second connectors, 32 and 34, and a passage 66 defined in the second connector 34 and extending parallel to the longitudinal axis thereof to a passage 68 defined in the third and fourth connectors, 36 and 38.

The first connector 32 is further provided with a cylindrical connecting piece 70 constituting in part a mechanism for detecting a damage of the laser transmitting tube 58. One end of the connecting piece 70 is fluidly connected with a flow rate sensor 72. The other end of the connecting piece 70 is connected to three passages defined in the second connector 34 and fluidly communicated in series; a circumferential passage 74, a passage 76 extended radially and inwardly from the circumferential passage 74, and passage 78 extending along the longitudinal axis of the second connector 34 and adjacent the distal ends of both the reduced portion 54 of the connector 34 and ferrule 56 inserted in the reduced portion 54.

A proximal end of the passage 78 is connected with a connecting tube 80 securely inserted therein. The connecting tube 80 has an inner diameter greater than the outer diameter of the laser transmitting tube 58, in which the laser transmitting tube 58 is extended. Also, a proximal end of the connecting tube 80 is connected with a protection tube 82. The protection tube 82, having an inner diameter greater than the outer diameter of the laser transmitting tube 58, surrounds and extends along the tube 58. The protection tube 82 together with the laser transmitting tube 58 extends through the flexible supply tube 16 into the hand instrument 14. Further, as best shown in FIG. 2B, in the hand instrument 14, the protection tube 82 is sealed at its distal end by a packing member 83 mounted on the laser transmitting tube 58.

The third connector 36 is provided with a cylindrical connecting piece 84 for discharge water. One end of the connecting piece 84 is fluidly connected with the water pump 22. The opposite end of the connecting piece 84 is fluidly connected through a passage 86 defined in the third connector 36, a connecting piece 88 connected at one end to the passage 86 and a water supply tube 90 connected at one end to the other end of the passage 88. The water supply tube 90, like protection tube 82, is extended through the flexible supply tube 16 into the hand instrument 14.

The fourth connector 38 includes a seal ring 92 therein. The seal ring 92 has an outer configuration corresponding to an inner configuration of the fourth connector 38 so that it can be secured therein. An O-ring is provided between the connector 38 and the seal ring 92 for sealing therebetween. A distal end of the seal ring 92 is connected with the flexible supply tube 16 so that an interior 94 of the: flexible supply tube 16 is fluidly connected with the passage 68 defined in the second, third, and fourth connectors, 34, 36, and 38.

Figure 3:
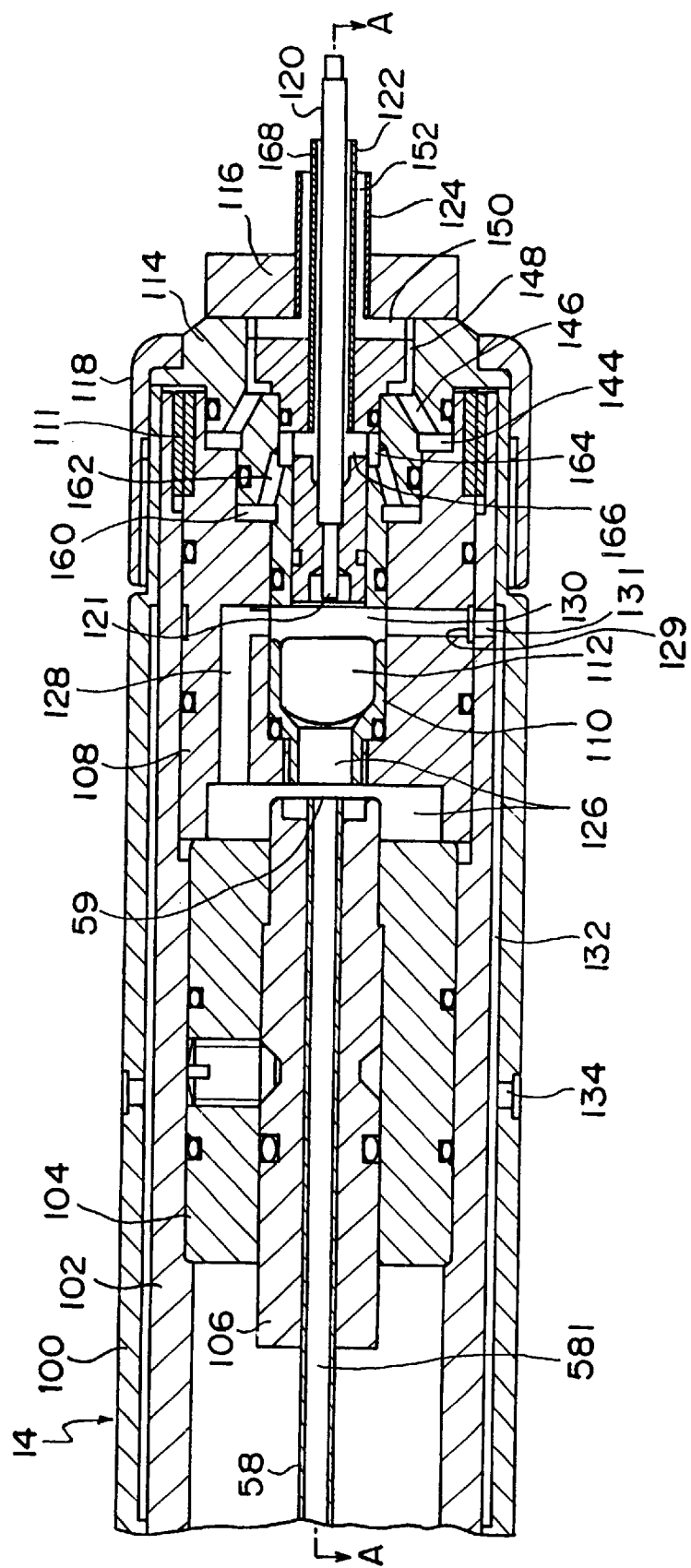
FIG. 3 is an enlarged cross sectional view of a part of a hand instrument in which the laser transmitting system of the present invention is incorporated.

FIG. 3 shows a distal end portion of the hand instrument 14. As shown in the drawing, the hand instrument 14 has a cylindrical outer casing 100 to be hand-held by the operator. The outer casing 100 is detachably mounted on a cylindrical second casing 102 inserted therein. The inner casing 102 holds a first cylindrical holder 104 retaining another cylindrical member or ferrule 106 therein. The ferrule 106 holds a distal end of the laser transmitting tube 58.

A cylindrical second holder 108 is also held in the distal portion of the inner casing 102 and arranged adjacent the first holder 104. The first and second holders, 104 and 108, are inserted together in the inner casing 102 through its distal end opening. A screw ring 111 having an external screw in its outer peripheral surface is engaged in and with an internal screw formed in an associated inner and distal end surface of the inner casing 102, so that the first and second holders, 104 and 108, are detachably secured in the inner casing 102. The second holder 108 accommodates therein a cylindrical lens holder 110 and a converging lens 112 held in the lens holder 110 so that an optical axis of the converging lens 112 positions on the longitudinal axis of the laser transmitting tube 58. A probe holder 114 is provided adjacent the distal end of the second holder 108 and in part inserted in the second holder 108. A cap nut 118 is mounted on the probe holder 114 and engaged at its internal screw with a corresponding external screw formed at the distal end of the outer casing 100. At assembling, the outer casing 100, probe holder 114, and the cap nut 118 are pre-assembled and then mounted detachably on the distal end portion of the inner casing 102.

A probe 116 is held with respect to the probe holder 114 in position with its external screw engaged with an internal screw formed in the probe holder 114. The probe holder 116 has an optical fiber 120, or second laser transmitting passage, preferably made from a quartz fiber, an inner tube 122 surrounding and extending along the optical fiber 120, and an outer tube 124 surrounding and extending along the inner tube 122, along a longitudinal axis of the laser transmitting tube 58. The optical fiber may be any one of commercially available optical fibers, each having an inner core and an outer clad.

The distal end, or outlet 59, of the laser transmitting tube 58 is fluidly connected with an atmosphere through a fist cooling chamber 126 adjacent the proximal surface of the converging lens 112 and defined between the first and second holders, 104 and 108, a second cooling chamber 130 defined between the converging lens 112 and the probe holder 114, a passage defined between the outer casing 100 and the inner casing 102, and a passage 134 defined in the outer casing 100.

It should be noted that, if the medical device 10 is a dental device, the passage 134 is preferably spaced away from the distal end of the hand instrument 14 so that air is discharged from the passage 134 outside a mouth of the patient.

Referring to FIGS. 2A, 2B, 3, and 4, the first holder 104 has a through hole 135 extending in parallel to its longitudinal axis in which an air supply tube 136 is retained. The proximal end of the air supply tube 136 is fluidly connected with a passage 138 defined inside the inner casing 102. Also, the passage 138 is fluidly connected with the interior 94 of the flexible supply tube 16. The distal end of the air supply tube 136 is securely inserted in a passage 140 defined in the second holder 108. The passage 140 is, connected to the atmosphere through a passage defined in the second holder 108, a circumferential passage 144 defined between the second holder 108 and the probe holder 114, a plurality of passages 146 defined in the probe holder 114, a plurality of passages 148 defined between the probe holder 114 and probe 116, a plurality of passages 150 defined in the probe 116 and extending radially, and a cylindrical passage 152 defined between the inner tube 122 and the outer tube 124.

Referring again to FIGS. 2A, 2B, 3, and 4, the first holder 104 has a hole 154 defined therein and extending in parallel to the longitudinal axis thereof. A connecting tube 91 connected with the water supply tube 90 is inserted in the hole 154. A distal end of the connecting tube 91 is inserted and fixed in a passage 156 defined in the second holder 108. The passage 156 is in turn connected with the atmosphere in the vicinity of the distal end of the optical fiber 120, through a passage 158 defined in the second holder 108, a circumferential passage 160 defined between the second holder 108 and the probe holder 114, a plurality of passages 162 defined in the probe holder 114, a circumferential passage 164 defined between the probe holder 114 and the probe 116, a plurality of passages 166 defined in the probe 116 and extending radially, and a cylindrical passage 168 defined between the optical fiber 120 and the inner tube 122.

In operation of the medical device 10 so constructed, with reference to FIG. 2A, laser generated in the laser generator 10 (see FIG. 1) is transmitted through the transparent window 50 and passage 48 into the interior of the laser transmitting tube 58 in the flexible supply tube 16. Referring to FIG. 3, laser transmitted to the hand instrument 14 is discharged from the outlet 59 of the laser transmitting tube 58, converged by the converging lens 112, and then transmitted into the inlet 121 of the optical fiber 120. Laser transmitted through the optical fiber 120 is emitted from the outlet of the optical fiber 120 against the desired surgical site.

As best shown in FIG. 2A, air for drying and cooling, supplied from the air pump 20 (see FIG. 1), is fed through the connecting tube 40, passages 42, 44, 46, and 48, and through the laser transmitting tube 58 surrounded by the flexible supply tube 16 into the hand instrument 14.

Next, as shown in FIG. 3, drying and cooling air discharged from the outlet 59 of the laser transmitting tube 58 cools down the outlet 59 as it passes therethrough. Then, the drying and cooling air impinges at the incident surface of the converging lens 112 in the first cooling chamber 126, adjacent the outlet 59 of the laser transmitting tube 58, thereby cooling down the incident surface of the converging lens 112 as well as cleaning off the foreign substances therefrom. Then, the drying and cooling air is transported through the passages, 126 and 128, into the second cooling chamber 130 where it impinges upon both the opposite surface of the converging lens 112 and the inlet 121 of the optical fiber 120, cleaning off the possible foreign substances therefrom. Afterwards, the drying and cooling air is transported from the second cooling chamber 130 through the circumferential passage 129 defined between the inner casing 102 and the second holder 108, and further through passages 131, 132, and 134 to the atmosphere.

Figure 4:
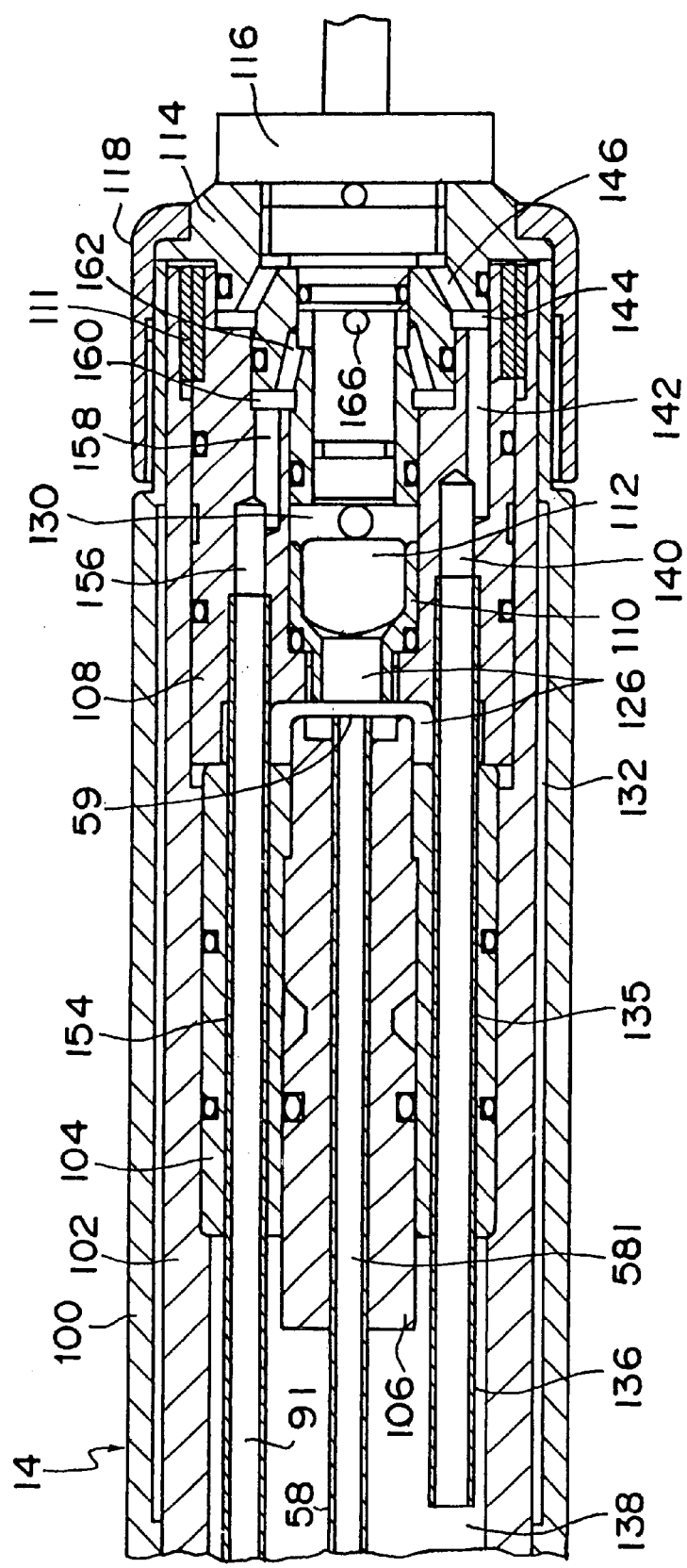
FIG. 4 is a an enlarged cross sectional view of the hand instrument in FIG. 3, taken along lines A—A.

As shown in FIGS. 2A, 3, and 4, the air, to be discharged to the surgical site, fed from the air pump 20 (see FIG. 1), is fed through the connecting tube 60 and passages 62, 64, and 66 into the interior 94 of the flexible supply tube 16. Then, as shown in FIG. 4, the air is fed into the passage 138 in the hand instrument 14 and through the supply tube 136, passages 140, 142, 144, and 146, passages 148 and 150 (see FIG. 3), and passage 152 defined between the inner tube 122 and the outer tube 124 and finally discharged toward a tip of the optical fiber 120.

Also, as; shown in FIG. 2A, 3, and 4, the water supplied from the water pump 22 (see FIG. 1) is transported through the connecting tube 84, passage 86, connecting tube 88 and water supply tube 90 into the flexible tube 16 toward the hand instrument 14. Next, as shown in FIG. 4, in the hand instrument 14, the water is supplied through the passages 156, 158, 160, and 162, passages 164 and 166 (see FIG. 3), and passage 168 defined between the optical fiber 120 and the inner tube 122, and finally discharged near the tip of the optical fiber 120 and mixed with the discharge air to be sprayed in the form of mist.

Figure 2:
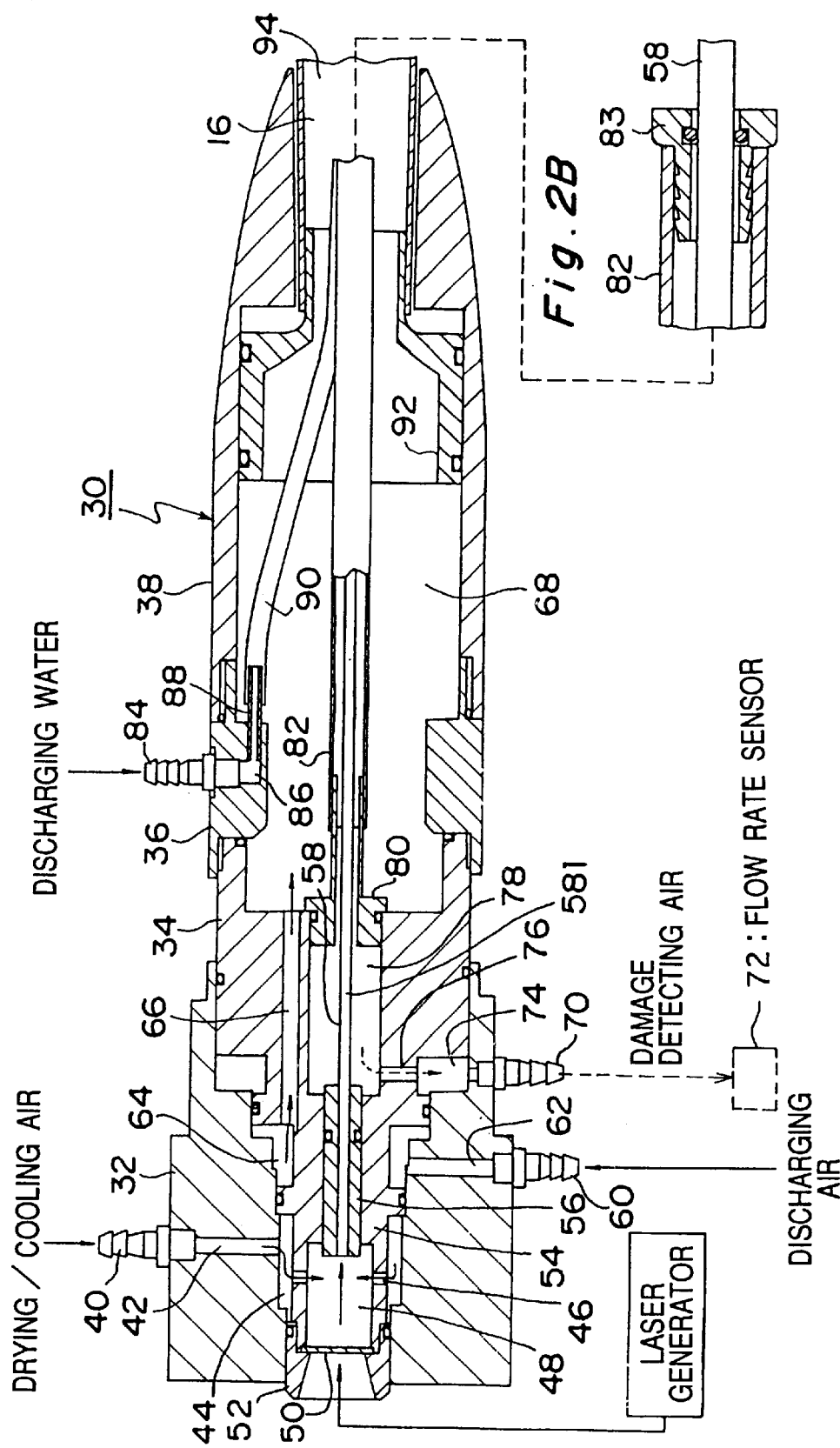
FIG. 2A is an enlarged cross sectional view of a connecting portion of a laser unit and a flexible supply tube.
FIG. 2B is an enlarged cross sectional view of a seal structure provided at a distal end of a protection tube.

In the event that the laser transmitting tube 58 for transmitting laser is damaged and then cracked, as shown in FIG. 2, the drying and cooling air running in the tube 58 leaks into the interior of the protection tube 82. The leaked air is then transported through passages 78, 76, and 74, and connecting tube 70 into the flow rate sensor 72. Once the sensor 72 detects a flow caused by the leaked air, it transmits a signal to the laser generator 18 to de-energize it, prohibiting further generation of laser.

Figure 5:
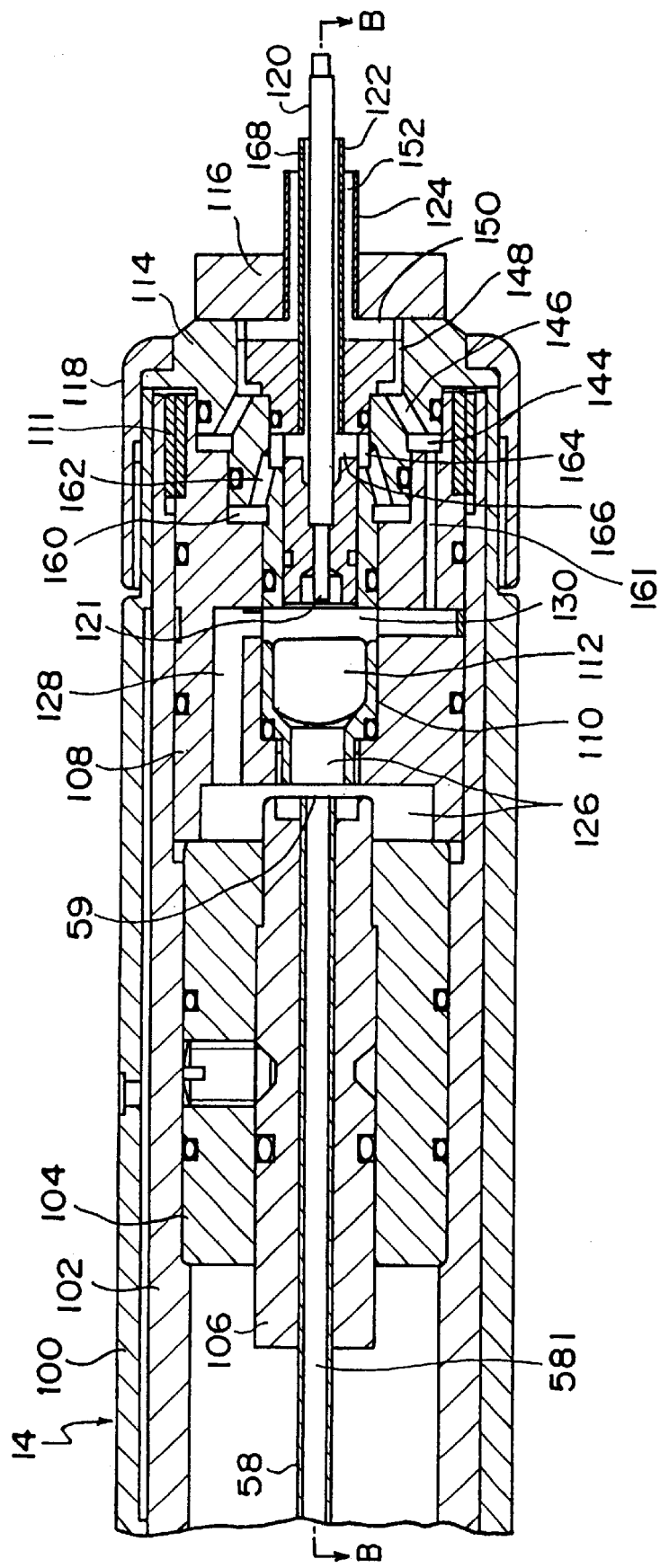
FIG. 5 is an enlarged cross sectional view of a part of the hand instrument in which the laser transmitting system of the second embodiment of the present invention is incorporated.
Figure 6:
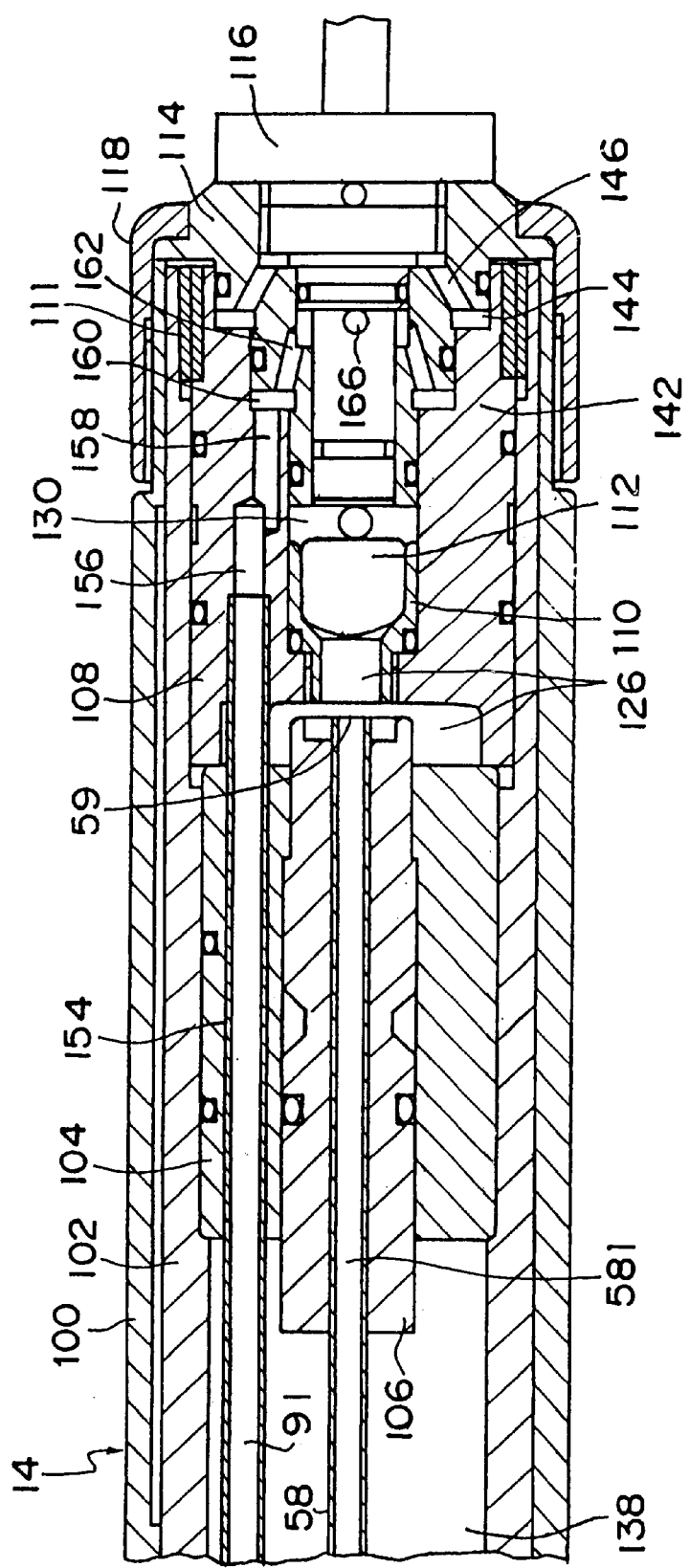
FIG. 6 is a an enlarged cross sectional view of the hand instrument in FIG. 5, taken along lines B—B.

FIG. 5 shows an enlarged sectional view of another embodiment of the hand instrument for use with the laser device, and FIG. 6 shows a partial cross sectional view of the hand instrument shown in FIG. 5, taken along the lines B—B. With this embodiment, the air supplied from the outlet 59 of the laser transmitting tube 58 is transported through the first cooling chamber 126, passage 128, second cooling chamber 130, passage 161, circumferential passage 144, passages 146 and 148, and then discharged in the direction which is identical to that laser is emitted from the optical fiber 120. The water is likewise guided through the passage 166 and then discharged and then mixed with the air, sprayed in the form of mist.

It should be noted that, in the first embodiment, the drying and cooling air fed into the first and then second cooling chambers, 126 and 130, and the air to be discharged are transported through respective ways, allowing the drying and cooling air to be fed into the cooling chambers without any interruption even when no air is discharged. In contrary to this, in the second embodiment, on the other hand, as can be seen from FIGS. 5 and 6, only one way is needed for the two airs, simplifying the routing of the airs in the hand instrument.

Also, with the medical device 10, air is supplied through the laser transmitting tube 58 (first passage) to cool the inlet 121 of the optical fiber 120 positioned on an optical axis of the tube 58. Therefore, no exclusive tube is needed in the flexible tube 16 or hand instrument 14 only for cooling down the inlet 121 of the optical fiber 120. This simplifies the piping and routing of air.

Although the converging lens 112 is provided between the outlet 59 of the laser transmitting tube 58 (first passage) and the inlet 121 of the optical fiber 120 (second passage) in the previous embodiments, the present invention is not limited thereto and it may be equally applied to the device in which no converging lens is provided.

Also, although in the embodiments described the optical fiber 120 (second passage) is positioned on the longitudinal axis of the laser transmitting tube 58 (first passage), the present invention is not limited thereto so far as the optical fiber 120 is optically connected with the laser transmitting tube 58. For example, the present invention envisions another embodiment in which one or more mirrors are provided between the outlet and inlet of two passages so that laser emitted from the outlet passage is reflected once or a: plurality of times and then into the outlet.

Further, although in the above-described embodiments the air to be discharged is fed through the passage 68 defined in the connecting piece 30, interior 94 of the flexible supply tube 16, and passage 138 in the hand instrument 14 into the connecting tube 136, it may be transported through a suitable tube that connects between the distal end of the passage 66 (see FIG. 2A) and the proximal end of the connecting tube 136 (see FIG. 4). In this instance, either or both ends of the tube 82 may be opened so that, when the laser transmitting tube 58 is damaged and then cracked, the drying and cooling air flows through the passages 68, 78, 76, and 74 into the connecting tube 70.

Furthermore, although the drying and cooling air is fed from the air pump 20, it may be supplied from another air pump.

Moreover, a dryer may be mounted in the piping system for the drying and cooling air for dehumidification.

It should be noted that the laser transmitting tube 58 may be made from any available tube capable of transmitting laser, made of materials such as metal and glass. The tube may be coated at its inner surface with both metal coating and dielectric coating provided on the metal coating. Materials of the dielectric coating may be polyimide, fluoroplastic, polysiloxane, polysilazane, cyclic polyolefin, metal-oxide, or metal-sulfide.

Also, in the embodiment described-above, although the second passage is made from the optical fiber, it may be a tube similar to the laser transmitting tube.

Further, although the wavelength of laser is not limited to above-described embodiment, Er:YAG laser is most preferably used due to its effective holing and perspiration for a hard tissue such as bone and tooth as well as its effective dissection, hemostasis, and perspiration for soft tissue such as muscle and for effective perspiration thereof.

Furthermore, the present invention is applicable in another laser transmitting system of various kinds of laser such as $CO_2$ laser, CO laser, and Nd:YAG laser.

In view of above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

It should be noted that the present application is based upon Japanese Patent Application No. 9-367532 which is entirely incorporated herein by reference.

What is claimed is:

1. A laser transmitting system for use with a laser device, comprising:

a first laser transmitting passage made from an optical hollow laser waveguide, including therein an interior opened at first and second ends of said first laser transmitting passage; and a second laser transmitting passage having a first end and a second end, said first end of the second laser transmitting passage being spaced away from but optically connected with said second end of said first laser transmitting passage, so that laser transmitted through said first laser transmitting passage is guided into said second laser transmitting passage while air is transmitted through said optical hollow laser waveguide of said first laser transmitting passage to impinge on said first end of said second laser transmitting passage.

2. The laser transmitting system as set forth in claim 1, further comprising:

an optical member positioned between said second end of said first laser transmitting passage and said first end of said second laser transmitting passage for guiding said laser transmitted from said second end of said first laser transmitting passage into said first end of said second laser transmitting passage; and an air passage defining a first chamber enclosing therein said second end of said first laser transmitting passage, a second chamber enclosing therein said first end of said second laser transmitting passage, and a passageway fluidly connecting said first and second chambers together, so that said air from said second end of said first laser transmitting passage is guided through said first chamber, said passageway, and said second chamber to impinge on said first end of said second laser transmitting passage.

3. A laser transmitting system as set forth in claim 2, further comprising:

an air passage having first and second ends, said first end of the air passage being positioned adjacent said first end of said second laser transmitting passage and said second end of said air passage being positioned adjacent said second end of said second laser transmitting passage, so that said air impinged on said first end of said second laser transmitting passage is further guided into said air passage and then discharged at around said second end of said second laser transmitting passage.

4. A hand instrument, comprising:

a casing including a first laser transmitting passage, made from a tube, including therein an interior opened at first and second ends of said first laser transmitting passage; and a second laser transmitting passage having a first end and a second end, said first end of the second laser transmitting passage being spaced away from but optically connected with said second end of said first laser transmitting passage, so that laser transmitted through said first laser transmitting passage is guided into said second laser transmitting passage while air is transmitted through said first laser transmitting passage to impinge on said first end of said second laser transmitting passage.

5. A hand instrument as set forth in claim 4, further comprising an air passage extending along said first and second laser transmitting passage and toward said second end of said second laser transmitting passage.

6. A hand instrument as set forth in claim 5, wherein said air passage is in part defined between said casing and said first laser transmitting passage.

7. A laser device, comprising:

a laser generator for generating laser;

an air supply for supplying air;

a hand instrument to be held by an operator; and a laser transmitting passage having a first laser passage made from an optical hollow waveguide and a second laser passage, said first laser passage being connected at one end thereof with both said laser generator and the air supply, optically and fluidly, respectively, and held at the other end thereof in said hand instrument, said second laser passage being held in the hand instrument with the one end thereof spaced away from but optically connected with said the other end of said first laser passage, so that said laser is transmitted from said laser generator through said first laser passage and through said second laser passage and said air is transported from said air supply through said optical hollow waveguide of said first laser passage to impinge on said one end of said second laser passage for cooling thereof.

8. A laser device as set forth in claim 7, further comprising:

a converging lens which converges said laser from said the other end of said first laser passage on said one end of said second laser passage; and a passageway which guides said air from said the other end of said first laser passage to said second end of said second laser passage.

9. A laser device as set forth in claim 8, wherein said passageway is further extended along said second laser passage so that said air impinged on said one end of said second laser passage flows out into the atmosphere in the vicinity of said the other end of said second laser passage.

* * * * *